United States Patent [19]
Easley

[11] Patent Number: 5,513,286
[45] Date of Patent: Apr. 30, 1996

[54] WHITE LIGHT DIMMER FOR FIBER OPTIC ILLUMINATION SOURCES

[75] Inventor: James C. Easley, St. Charles, Mo.

[73] Assignee: Syntec, Inc., Winfield, Mo.

[21] Appl. No.: 255,660

[22] Filed: Jun. 8, 1994

[51] Int. Cl.⁶ .................................................. G02B 6/26
[52] U.S. Cl. .................. 385/19; 385/25; 385/140; 362/32; 359/227
[58] Field of Search ................... 385/23, 31, 19, 385/139, 140, 25, 73, 77; 362/32; 359/227

[56] References Cited

U.S. PATENT DOCUMENTS

| | | | |
|---|---|---|---|
| 4,322,129 | 3/1982 | Takahashi et al. | 385/1 X |
| 4,376,566 | 3/1983 | Blackington | 385/19 |
| 4,556,280 | 12/1985 | Bagby | 358/19 |
| 4,560,238 | 12/1985 | Mori | 385/16 |
| 4,591,231 | 5/1986 | Kaiser et al. | 385/19 X |
| 4,738,506 | 4/1988 | Abendschein et al. | 385/19 |
| 4,757,426 | 7/1988 | Scheller et al. | 362/20 |
| 4,778,254 | 10/1988 | Gilliland, III et al. | 385/23 X |
| 4,836,636 | 6/1989 | Obara et al. | 385/23 X |
| 5,006,965 | 4/1991 | Jones | 362/32 |
| 5,101,468 | 3/1992 | Chiu | 385/115 |
| 5,268,977 | 12/1993 | Miller | 385/33 |
| 5,434,756 | 7/1995 | Hsu et al. | 362/32 |

*Primary Examiner*—Rodney B. Bovernick
*Assistant Examiner*—Hemang Sanghavi
*Attorney, Agent, or Firm*—Polster, Lieder, Woodruff & Lucchesi

[57] ABSTRACT

The present invention provides a method and apparatus for dimming the white light received by an optical fiber. The apparatus is a cover having a thin edge and a flat surface for application to the optical fiber commencing at the fiber rim.

10 Claims, 4 Drawing Sheets

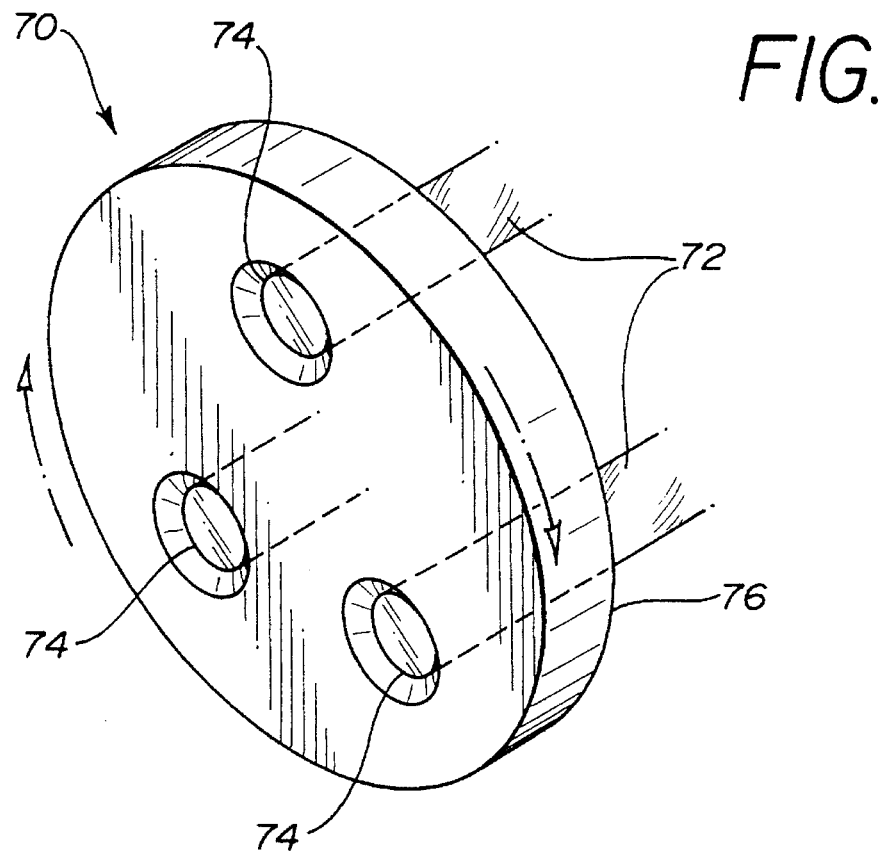
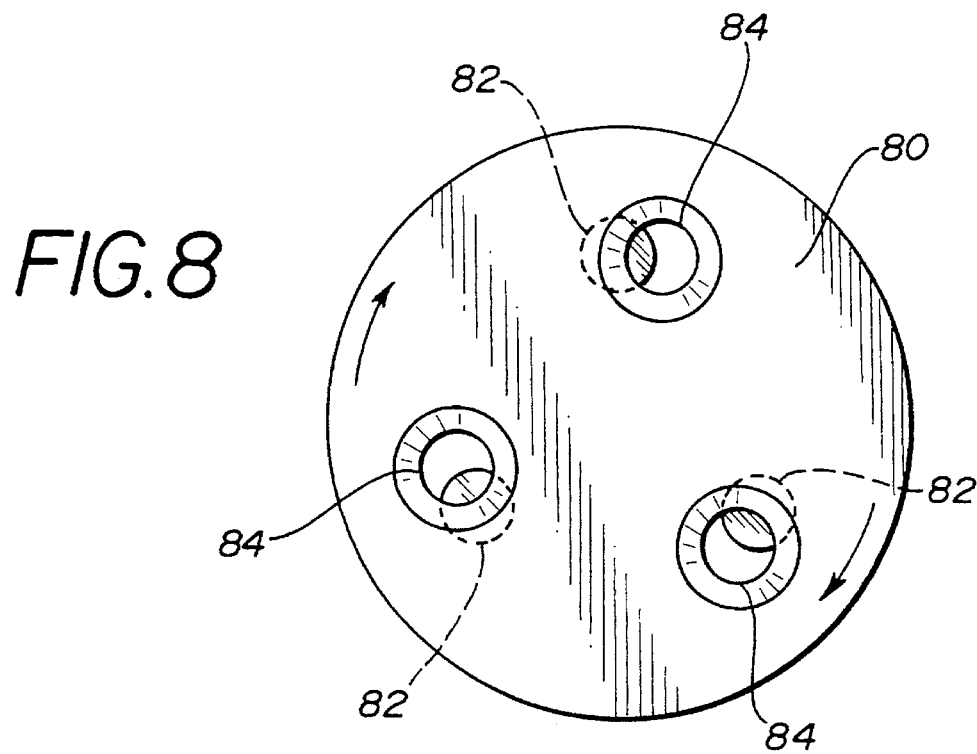

WHITE LIGHT DIMMER FOR FIBER OPTIC ILLUMINATION SOURCES

BACKGROUND OF THE INVENTION

In many types of microsurgery, particularly ophthalmic retinal surgery, a source of light is required. The light source is used to illuminate the surgical field. In many surgical procedural instances, the surgical field is relatively open and hence focused lamps above the surgical area will suffice to illuminate the surgical field adequately. However, in retinal surgery, the surgical field is inside the globe of the eye. External light sources tend to cause reflections from the cornea of the eye thus distorting the surgical field. Furthermore, when an external light source is used, the aperture available for penetration of the light into the surgical field is limited by the pupil of the eye. For these reasons, it is common practice to use a fiber optic instrument to deliver light to the inside of the eye. By use of such fiber optic instruments, corneal reflections and/or burns are substantially eliminated and the light may be pointed in any desirable direction.

The amount of light required to allow adequate viewing of the surgical field within the eye is considerable. There are several factors which contribute to this. For instance, the inside of the eye does not readily reflect light to surrounding areas. Even though a healthy cornea may be present, there will be some reflection from its inside surface. The same situation applies to the lens. The available light for viewing is reduced. With respect to a cataractous eye or when an unhealthy cornea is present, some of the light is absorbed and/or scattered. In instances where the eye has experienced a hemorrhage, the fluid of the eye, known as the vitreous humor, will tend to be cloudy. This also will reduce the usable light for visualization.

In many instances, a surgeon operates using a binocular microscope whereby the magnification of the surgical sight can be as high as twenty-five times (25×). Generally in hospitals, the microscope will have other observation ports for an assistant to see and/or for a video camera. As a result, the apparent brightness to the surgeon is reduced considerably.

To overcome the above difficulties, fiber optic instruments have been developed such that the instrument producing the light casts the light directly on the surgical site. Sometimes it has been found desirable to combine the fiber optic instrument with another instrument. Such combinations can allow the surgeon to use both hands to manipulate the tissues instead of one hand to manipulate tissues and the other to direct the light. These multi-function instruments generally use a smaller optical fiber.

The incision made for insertion of the instrument is as small as possible. Most light sources available for illumination of the optical fibers have a focal point that is much larger than even the largest optical fiber in use. Consequently, the output of the fibers is directly proportional to the cross sectional area of the fiber. In other words, in a fiber having a diameter of 0.03", the light output will be 2.25 times the output of a fiber having a diameter of 0.02". The just mentioned fiber sizes are exemplary of typical fiber sizes used for illuminated optical fibers.

During surgery, the surgeon relies upon the color of the different parts of the eye to diagnose either the condition of the tissue or perhaps the effectiveness of a prior treatment. For this reason, it is important that the color of the light is white. In fact, if the light is slightly yellow or slightly blue, the variance from the white light will tend to color the tissues making it difficult to provide an accurate diagnosis.

Developments have enhanced the intensity of the white light used to illuminate optical fibers. Too high an intensity of light delivered to the eye can result in phototoxicity to the eye. Although studies have addressed the problem of phototoxicity to the eye, specific acceptable levels of intensity have not been identified. Consequently, it becomes more important to have the ability to adjust the intensity of the light by dimming the light without distortion of the light. In order for a method of dimming the light to be satisfactory, it would be necessary for a method to allow a change in the intensity of at least fifty percent (50%) as well as retaining the white light color of the light as if no dimming had been made. The angle of the light impinging on the optical fiber directly affects the output angle of the light from the illuminated fiber. Thus, the aperture of the source of light for illumination of the fiber should remain the same even if the intensity of the light produced by the optical fiber is dimmed.

Several attempts have been made to dim the light intensity available to the optical fiber. One method used by manufacturers is to limit the electrical current available to the source lamp filament. This results in a temperature change of the filament and as a result, the color of the light is changed to a light which is more red. In another attempt, a circular disk is used that is placed perpendicular to the light axis and between the lamp and the optical fiber, the disk has a decreasing width slot in order to decrease the aperture of the source light gradually. Using such a disk causes the light gradually to get blocked by the edges of the slot in the disk. The result is not an actual dimming of the light intensity, but a change in the aperture. The result causes the outer edges of the output circle of the optical fiber to become smeared and then become dark. The center of the output pattern from the fiber is not reduced in intensity.

In still another attempt at dimming the light, a disk is placed in the light path which disk has a series of holes etched through it, as the disk is turned, the density of the holes decreases. The result of using such a method is creation of a series of dark concentric rings in the output of light by the optical fiber. As the disk is turned, the location of the rings changes but the rings never disappear. Here again, the intensity of the light outside of the these rings does not change as the "dimming" mechanism is used. This is caused by a disproportionate blocking of light rays at various angles to the fiber axis. The disk will block more rays at a given angle to the fiber as evidenced by the dark rings in the output. Since the actual hole spacing changes circumferentially, the angular relationship changes as the disk is turned causing the apparent motion of the rings as the source of light is dimmed. Another method of attempting to dim the light source is by moving a light source lamp away from the fiber end. This results in an aperture change because as the lamp is moved away, the output angle narrows.

The present invention provides a dimmer which has no effect on the aperture of the light source for illumination of the optical fiber. Hence, the dimmer of the present invention truly dims the light intensity provided by the illuminated optical fiber.

SUMMARY OF THE INVENTION

One of the objects of this invention is to provide an improved white light dimmer.

Another object of the invention is to provide a white light dimmer having a simplified but effective construction.

Yet another object of this invention is to provide a dimmer that operates effectively in retinal surgery applications.

Still another object of this invention is to provide an improved method of dimming white light.

The present invention provides a white light dimmer for an illuminated optical fiber comprising a cover having sufficient overall dimension to cover the end of the optical fiber. The cover has a first flat surface terminating in at least one thin edge and a second non-flat surface terminating in the at least one thin edge. A varying thickness of material is between the first and second surfaces. The at least one thin edge has a thickness less than about 0.01" and has a length greater than the diameter of the optical fiber. It has been discovered that by covering the receiving end of the optical fiber partly with a cover, the light is dimmed without producing any of the adverse effects as discussed above.

An important factor of the present invention is that a thin edge be the first part of the cover to come in contact with the rim of the optical fiber at the time that the cover is first commencing to cover a part of the illuminated optical fiber. It is also important that the surface in contact with the rim of the optical fiber is flat so that while the cover is being placed in position gradually, there is no light seepage around the cover.

The second surface of the cover may vary in configuration according to convenience and preferred design. For instance, the second surface may have a configuration to allow gripping of the surface to assist in sliding the cover on its flat surface gradually over the end of the optical fiber. The upper surface tapers away from the thin edge in such a manner as to increase gradually the thickness of the material between the first and second surfaces. As the thickness increases away from the thin edge, the angle formed by the first and second surfaces at the point of contact at the thin edge, should be less than the critical entrance angle of light to the fiber. The angle should be less than 70°, preferably about 45°. This prevents any distortion of the source light as it reaches the optical fiber end. How thin the edge needs to be is determined by how sensitive the aperture change of the source light actually is in a given situation. From a practical standpoint for most purposes up to about 0.01" is satisfactory. The edge thinness could be maintained throughout the entire cover however, such a thin edge tends to be fragile and it is perceived that a greater thickness than the thin edge is needed to insure a stable and more rugged product. Aside from the thin edge and the flat surface, no particular geometry of the product is required.

The invention further provides a method for dimming the intensity of white light provided to an optical fiber. The method comprises placing a thin edge of an optical fiber cover having a flat surface terminating in the thin edge against a rim of the optical fiber at the end receiving illumination, and then gradually covering the end receiving illumination with the flat surface of the cover until the desired dimming is achieved. Any form of motion of the cover will work so long as a thin edge of the cover initially contacts the rim and the cover proceeds in a motion such that the flat surface gradually covers at least a portion of the end of the optical fiber. Either a linear motion or a circular motion across the fiber end may be used. A drive mechanism for the cover then may employ either a reciprocating motion or a rotational motion.

BRIEF DESCRIPTION OF THE DRAWINGS

In the drawings,

FIG. 7 is a perspective view of a still further embodiment of the present invention;

FIG. 8 is a top view of the embodiment of FIG. 7; and

DETAILED DESCRIPTION OF THE INVENTION

Figure 1:
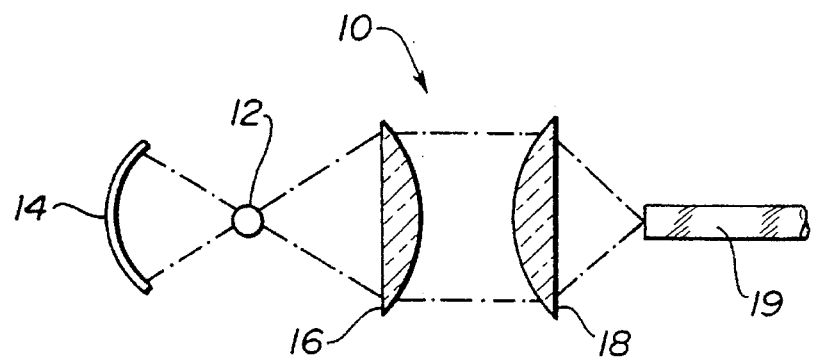
FIG. 1 is a schematic illustrating formation of a source of light suitable for illuminating an optical fiber.

FIG. 1 is a schematic illustrating a satisfactory mechanism 10 for providing a light source to an optical fiber 19. The mechanism 10 has a lamp 12 which provides light to a mirror 14 and a convex lens 16. The light from the mirror 14 and the lens 16 is then passed to another convex lens 18 in a mirror like position with respect to the first convex lens 16. The convex lens 18 directs the light as well as intensifies the light to the tip of the optical fiber 19. This mechanism 10 illustrates only one kind of mechanism used to provide light sources to the optical fiber such as the fiber 19.

Figure 2:
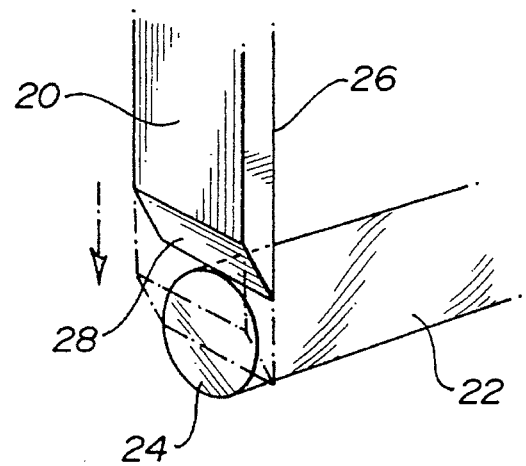
FIG. 2 depicts one embodiment of the present invention.
Figure 3:
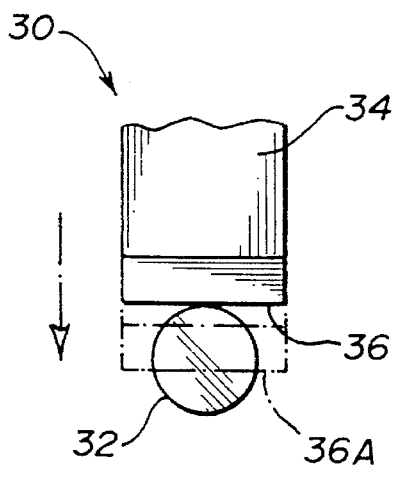
FIG. 3 is a front elevational view of the embodiment of FIG. 2.
Figure 4:
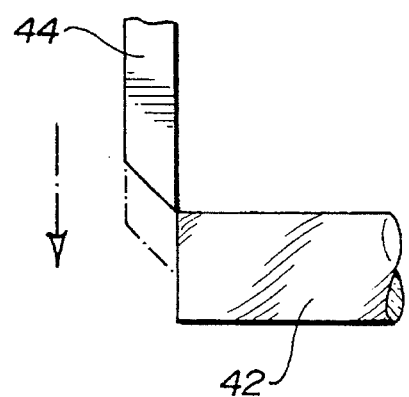
FIG. 4 is a side elevational view of the embodiment of FIG. 2.

FIG. 2 illustrates one embodiment of the present invention whereupon a rectangular dimmer cover 20 is provided with a thin edge 28 and a flat surface 26. The thin edge 28 of the dimmer cover 20 is placed at an edge 21 of the rim of the optical fiber 22 and commences to cover the opening 24 of the optical fiber 22 by a downward movement of the cover 20. FIG. 3 depicts the fiber and cover of FIG. 2 in a front elevational view. The cover 30 has a top surface 34 and a thin edge 36. As the thin edge is lowered to cover the optical fiber 32, the thin edge assumes a new position identified as 36A. FIG. 4 depicts the fiber and cover of FIG. 2 in a side elevational view showing the cover 44 and the fiber 42.

Figure 5:
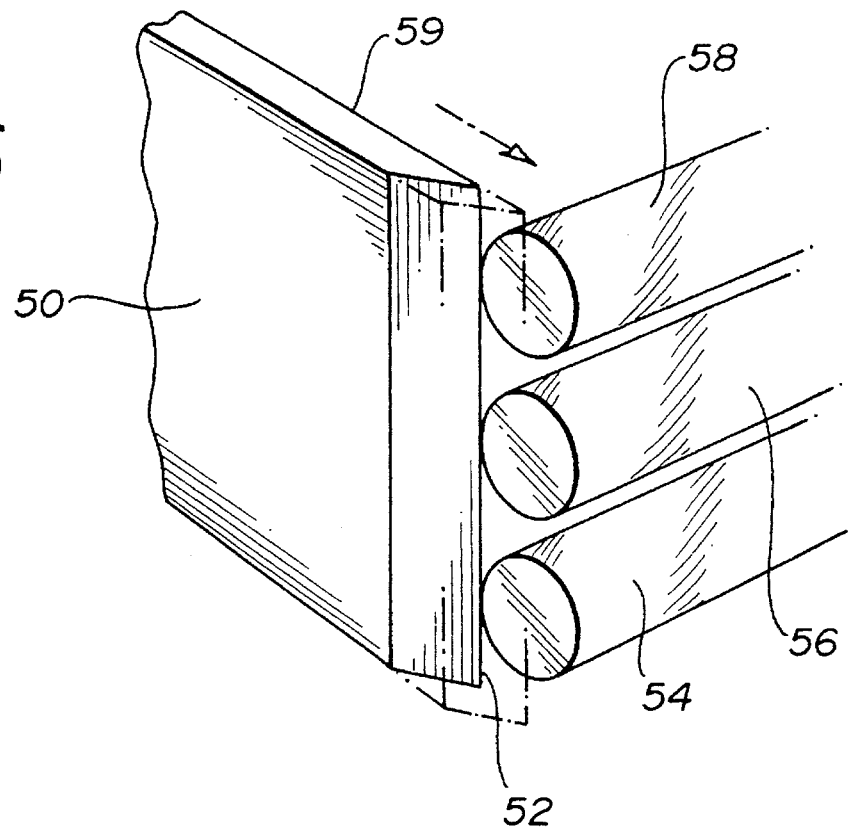
FIG. 5 is a perspective view of another embodiment of the present invention.

FIG. 5 is a perspective view of a further embodiment of the invention. The cover 50 is shown in a position commencing the covering of three optical fibers 54, 56 and 58. The cover 50 is shown where the thin edge 52 is about to be moved linearly so as to begin covering all three fibers 54, 56 and 58 with the flat side 59 of cover 50.

Figure 6:
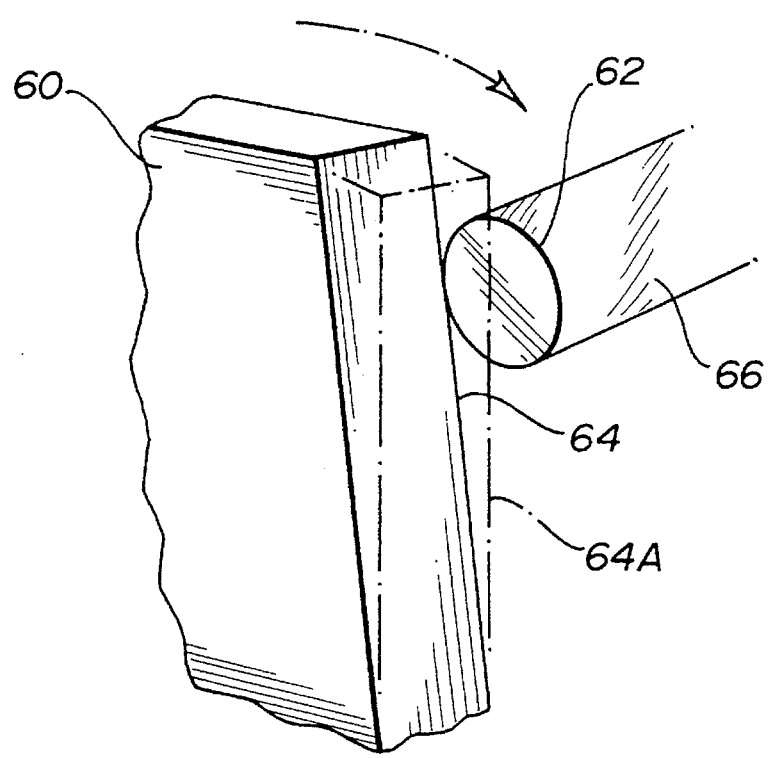
FIG. 6 is a perspective view of a still further embodiment of the present invention.

FIG. 6 depicts a cover 60 with a thin edge 64 about to be rotated such that the thin edge will commence covering the rim Step 62 of the optical fiber 66 resulting in the thin edge taking the position at 64A. FIG. 5 depicts a linear motion of the cover whereas FIG. 6 shows an arcuate motion by rotation of the cover.

FIG. 7 depicts a cover 70 shown in position above three fibers 72. Circular openings slightly larger than the fiber ends are above each fiber and corresponding holes in the cover allow the illuminating light to enter the fiber ends. The rims of the holes are thin edges 74. As the cover is rotated over the fibers, the thin edges 74 will begin to cover the fibers with the flat surface 76.

In FIG. 8, the cover of FIG. 7 is depicted in a top view showing the cover 80 rotated slightly clockwise partially covering the optical fibers 82. The rims 84 of the holes in the cover have moved sufficiently such that the flat surface of the cover has partially covered the optical fiber ends.

Figure 9:
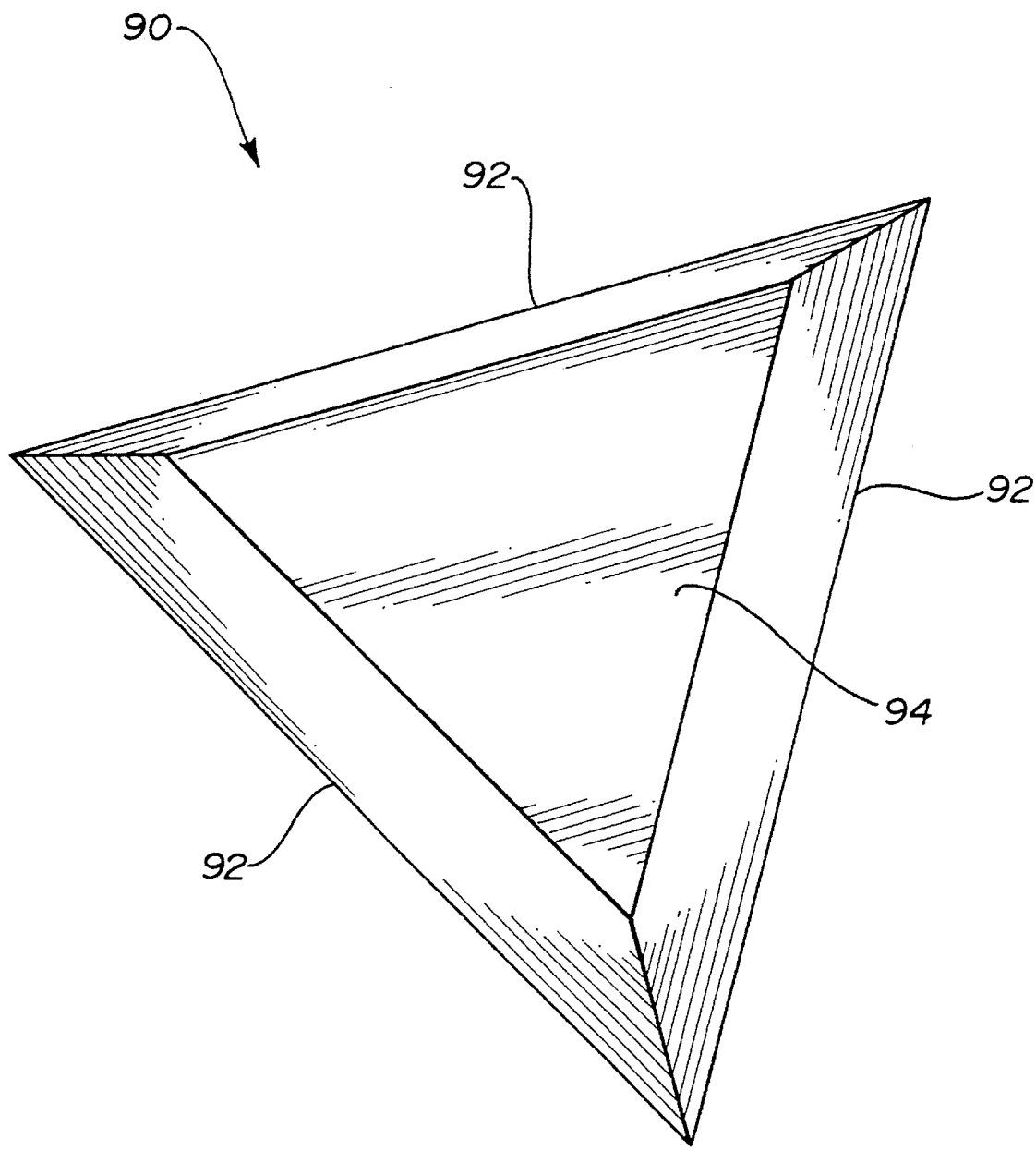
FIG. 9 is a perspective view of another embodiment of the present invention.

FIG. 9 depicts a perspective view of another embodiment of the present invention wherein a cover 90 is a triangular shape having three straight sides 92 and a top surface 94. The triangle may use a straight side to commence covering an optical fiber or any of the three points of the triangle may commence covering the optical fiber in particular instances where a certain kind of dimming is desired.

As shown by the FIGS. discussed above, the geometry of the cover is not critical to the performance of the cover. The performance of the mechanism is unaffected by how thick the cover is except that the angle formed by the first surface and the second surface intersection at the thin edge needs to be less than the critical entrance angle of light to illuminate the fiber. The sharpness of the thin edge is determined by how sensitive the requirement for the dimming of the light is in a given application. For most purposes, the thickness of the thin edge can be tolerated up to about 0.01" and preferably less than 0.007". Conceivably, the cover could be of the same thickness throughout provided that thickness does not exceed what is required at the thin edge. However, for materials to be rendered less than 0.01" will generally make them fragile and consequently easily broken.

A circular cover having at least one hole in size of an area at least equal to the area of the cross section of the optical fiber provides a highly desirable cover. The cover may be easily rotated in a clockwise or counterclockwise position allowing a thin edge in the form of an arc gradually to cover the optical fiber end. The circular configuration permits fine tuning of the dimming provided by the cover. Multiplicities of fibers may be dimmed simultaneously by having more than one cover or by having the cover structured in such a way with its relationship to the fibers that more than one fiber is covered simultaneously by movement of the cover. Most optical fibers have a diameter up to about 1 mm. When an optical fiber is to have a cover wherein a hole in the cover is utilized, the hole should range up to about 1.25 mm in diameter or sufficiently large to permit the entire optical fiber to be viewed through the hole. Around each hole in the cover is a beveled region wherein a thin edge is supplied which first comes passes over the rim of the optical fiber when the cover is moved to commence covering of the fiber. The configuration of the thin edge can take shape so as to make the optical fiber illumination dim fast at the beginning and then slow gradually or in such a way as to have the dimming commence gradually and become faster as the cover is moved across the optical fiber end.

The covers of the present invention may be made of coated glass, plastic, metal or other formable material which will permit the shape of the cover to remain even after many times of use.

I claim:

1. A white light dimmer for an illuminated optical fiber wherein an aperture of a source of converging white light for the illumination of the fiber remains the same while the intensity of the light produced by the optical fiber is dimmed comprising:

a cover having a first flat surface terminating in at least one thin edge, a second non-flat surface terminating in the at least one thin edge, and a varying thickness of material between the first and second surfaces;

wherein the first flat surface of the cover touches and gradually partially covers a receiving end of the illuminated optical fiber, and wherein the angle formed by the intersection of the first surface and the second surface at the thin edge is less than the critical entrance angle of the source light to illuminate the optical fiber; and said at least one thin edge having a thickness less than about 0.01" and having a length greater than the diameter of the optical fiber.

2. The cover of claim 1 wherein the thickness of the material varies from about 0" to about 1" in thickness.

3. The cover of claim 1 wherein the configuration of the cover is substantially rectangular with one thin edge.

4. The cover of claim 3 wherein the angle of the increase in thickness from the thin edge is less than about 70°.

5. The cover of claim 4 wherein the angle of thickness increasing from the thin edge is about 45°.

6. The cover of claim 1 wherein the configuration of the cover is substantially circular where the circumference is a thin edge.

7. The cover of claim 1 wherein the cover has at least one circular opening formed in it, the material thickness of the cover about the opening being formed into a thin edge.

8. The cover of claim 1 wherein the configuration of the cover is substantially triangular having at least one thin edge.

9. The cover of claim 1 wherein the thin edge has a thickness less than 0.007".

10. The cover of claim 1 having sufficient overall dimension to at least equal the cross sectional area of the optical fiber.

* * * * *